US005285679A

United States Patent [19]
Jackson et al.

[11] Patent Number: 5,285,679
[45] Date of Patent: Feb. 15, 1994

[54] QUANTIFICATION OF BLAST FURNACE SLAG IN A SLURRY

[75] Inventors: William E. Jackson, Sugar Land; Thomas E. Murray, Missouri City; Arthur H. Hale, Houston, all of Tex.

[73] Assignee: Shell Oil Company, Houston, Tex.

[21] Appl. No.: 964,981

[22] Filed: Oct. 22, 1992

[51] Int. Cl.$^5$ .......................... G01N 5/04; G01N 23/20
[52] U.S. Cl. ...................................... 73/61.72; 378/71; 378/86; 422/285; 436/4; 501/8
[58] Field of Search ................ 73/61.72, 61.41, 61.43, 73/61.71; 378/71, 73, 86, 89; 422/285, 245; 436/4; 264/29.2; 501/8

[56] References Cited

U.S. PATENT DOCUMENTS

| | | |
|---|---|---|
| 2,649,160 | 8/1953 | Williams et al. . |
| 2,880,096 | 3/1959 | Hurley . |
| 2,895,301 | 7/1959 | Casagrande et al. . |
| 2,938,353 | 3/1960 | Vorenkamp . |
| 2,961,044 | 11/1960 | Shell . |
| 3,021,680 | 2/1962 | Hayward . |
| 3,168,139 | 2/1965 | Kennedy et al. . |
| 3,412,564 | 11/1968 | McClintock . |
| 3,499,491 | 3/1970 | Wyant et al. . |
| 3,557,876 | 1/1971 | Tragesser . |
| 3,670,832 | 6/1972 | Striegler . |
| 3,675,728 | 7/1972 | Faulk et al. . |
| 3,712,393 | 1/1973 | Sheldahl et al. . |
| 3,724,562 | 4/1973 | Striegler . |
| 3,820,611 | 6/1974 | King . |
| 3,835,939 | 9/1974 | McEntire . |
| 3,887,009 | 6/1975 | Miller et al. . |
| 3,893,333 | 7/1975 | Sunahara et al. ................... 73/61.72 |
| 3,962,878 | 6/1976 | Hansen . |
| 4,037,424 | 7/1977 | Anders . |
| 4,057,116 | 11/1977 | Striegler . |
| 4,215,952 | 8/1980 | Baardsen . |
| 4,252,471 | 2/1981 | Straub . |
| 4,335,980 | 6/1982 | DePriester . |
| 4,338,134 | 7/1982 | Graf zu Munster . |
| 4,425,055 | 1/1984 | Tiedemann . |
| 4,427,320 | 1/1984 | Bhula . |
| 4,460,292 | 7/1984 | Durham et al. . |
| 4,634,462 | 1/1987 | Fish et al. ....................... 422/245 X |
| 4,664,843 | 5/1987 | Burba, III et al. . |
| 4,668,128 | 5/1987 | Hartley et al. . |
| 4,704,899 | 11/1987 | Burr et al. .......................... 73/61.72 |
| 4,720,214 | 1/1988 | Brasted et al. . |
| 4,760,882 | 8/1988 | Novak . |
| 4,761,183 | 8/1988 | Clarke . |
| 4,790,954 | 12/1988 | Burba, III et al. . |
| 4,853,349 | 8/1989 | Martin ....................................... 501/8 |
| 4,880,468 | 11/1989 | Bowlin et al. . |
| 4,897,119 | 1/1990 | Clarke . |
| 4,898,723 | 2/1990 | Suto et al. ...................... 264/29.2 X |
| 4,913,585 | 4/1990 | Thompson et al. . |
| 4,942,929 | 7/1990 | Malachosky et al. . |
| 4,991,668 | 2/1991 | Rehm et al. . |
| 5,016,711 | 5/1991 | Cowan . |
| 5,026,215 | 6/1991 | Clarke . |
| 5,058,679 | 10/1991 | Hale et al. . |
| 5,086,850 | 2/1992 | Harris et al. . |
| 5,105,885 | 4/1992 | Bray et al. . |
| 5,106,423 | 4/1992 | Clarke . |
| 5,121,795 | 6/1992 | Ewert et al. . |
| 5,123,487 | 6/1992 | Harris et al. . |
| 5,125,455 | 6/1992 | Harris et al. . |
| 5,127,473 | 7/1992 | Harris et al. . |

FOREIGN PATENT DOCUMENTS 85-144069/24 7/1983 Japan .

OTHER PUBLICATIONS

"Deep Cement Mixing Experience in Japan", by G. Dennis et al, Copyright 1985 Seabed Strengthening Symposium, Denver, Colo., Jun. 4, 1985, TP 85-5.

(List continued on next page.)

Primary Examiner—Robert J. Warden
Assistant Examiner—E. Leigh Dawson

[57] ABSTRACT

A method is provided to determine the concentration of an amorphous material such as blast furnace slag in a slurry such as drilling fluid, completion fluid fluids. A sample is annealed at a temperature between about 800° C. and about 1000° C. for a time period of about six hours to form crystals from the amorphous material, and the sample along with a known amount of a standard is then analyzed by X-ray diffraction. This method is particularly useful in determining the amount of blast furnace slag in a drilling fluid prior to conversion of the drilling fluid to a wellbore cement slurry by addition of additional blast furnace slag.

6 Claims, 2 Drawing Sheets

OTHER PUBLICATIONS

"Mud Disposal: An Industry Perspective", Hanson et al, Drilling, May 1986, pp. 16–21.

"Waste Minimization Program Can Reduce Drilling Costs", Hall et al, Oryx Energy Co., Houston, Tex., Oil & Gas Journal, Jul. 1, 1991, pp. 43–46.

"Phosphoric Acids and Phosphates", Kirk–Othmer Enc. of Chemical Technology, 3rd Ed., vol. 17, p. 477.

"Conversion of Drilling Fluids to Cements with Blast Furnace Slag-Performance Properties and Applications for Well Cementing", SPE Paper 24575 (Oct. 4, 1992) by Cowan et al.

"Quantitative Interpretation of X-Ray Diffraction Patterns of Mixtures. I. Matrix-Flushing Method for Quantitative Multicomponent Analysis" by Frank H. Chung, J. Appl. Cryst. (1974) 7, pp. 519–525.

QUANTIFICATION OF BLAST FURNACE SLAG IN A SLURRY

FIELD OF THE INVENTION

The present invention relates to a method to determine the amount of an blast furnace slag in a sample.

BACKGROUND OF THE INVENTION

Tragesser, in U.S. Pat. No. 3,557,876 and Nahm in U.S. patent application Ser. No. 691,905, disclose the addition of pozzolan to drilling fluids. These pozzolans, when included in drilling fluids, provide a filter cake to prevent fluid loss from the wellbore wherein the filter cake has certain desirable properties. The filter cakes deposited from pozzolan-containing drilling muds can be made to be compatible with cements, and the filter cake itself can be converted into a cementitious material that bonds well with both wellbore cement and the formation. This eliminates problems of contamination of cement by incompatible filter cakes, and eliminates the need to displace mud and filter cake prior to cementing. Pozzolan, according to Tragesser, includes fly ash, flue dust, certain boiler and furnace slags, burnt ground brick, by-products of certain industrial processes, pumicites or volcanic ashes, pumice or pumice stones, obsidian, scoria, tuffs, some of the andesites, diatomites, cherts, shale, clays and pure opal. Nahm discloses particular advantages for the use of blast furnace slag as the pozzolan.

An improvement to the methods of using pozzolan-containing drilling muds is to convert the pozzolan-containing drilling muds directly to cementing slurries. Converting drilling muds directly to cementing slurries eliminates the need to dispose of used muds, eliminates the need to add some materials to the cement that are already present in the muds, such as fluid loss additives, and further improves compatibility of the muds with cementing slurries. Mud-based cements such as these are disclosed in U.S. Pat. Nos. 3,168,139; 3,499,491; and 5,058,679. U.S. Pat. No. 5,058,679 discloses a conversion of drilling mud directly to a cement slurry by adding blast furnace slag; curing agents such as sodium hydroxide, potassium hydroxide, zinc carbonate, or sodium carbonate; and optionally set control additives. The use of blast furnace slag cements instead of Portland cements significantly lowers cement costs, and further improves compatibility with pozzolan-containing drilling muds.

Determination of the amount of blast furnace slag in the drilling mud and in the cement slurry becomes important when blast furnace slag-containing drilling mud is converted to blast furnace slag cement. The amount of blast furnace slag remaining in mud will vary depending upon many factors. The amount of blast furnace slag in the final cementing slurry must be controlled to accomplish an acceptable slurry rheology, set time, and set cement properties.

An acceptable method was not previously known to determine the amount of an amorphous material such as slag in a slurry such as drilling muds, completion fluids, workover fluids or cement slurries. Such a method will be beneficial in conversion of muds containing amorphous materials such as blast furnace slag into blast furnace slag cement slurries.

Relative weight fractions of crystalline materials can be readily obtained by well-known X-ray diffraction techniques. But presence of a significant portion of an amorphous material such as blast furnace slag prevents obtaining useful information by existing X-ray diffraction techniques. X-ray diffraction has therefore not been a useful method in determination of the amounts of amorphous material in slurries such as cement slurries, drilling muds, completion fluids or workover fluids.

Use of X-ray diffraction as a quantitative analysis method for crystalline solids is disclosed by, for example, F. H. Chung, "Quantitative Interpretation of X-ray Diffraction Patterns of Mixtures. I. Matrix Flushing Method for Quantitative Multicomponent Analysis," *J. Appl. Crystallogr.*, 7, p. 519-25 (1974). This method is not useful when a significant amount of amorphous material is present.

It is therefore an object of the present invention to provide an analytical method capable of determining the amount of an amorphous material such as blast furnace slag in a sample such as cement slurry, drilling mud, completion fluid, and workover fluid.

SUMMARY OF THE INVENTION

This and other objects are accomplished by a process to determine the concentration of amorphous blast furnace slag in a sample comprising the steps of: providing a known quantity of the sample; annealing the known quantity of the sample at a temperature of between about 800° C. and about 1000° C. for a time period of about two hours or greater thereby converting the amorphous blast furnace slag to a crystalline composition comprising melilite; adding a known quantity of a standard to the annealed sample; determining the amount of weight loss from the sample resulting from the annealing of the sample; measuring the X-ray diffraction peak intensity of the annealed sample for a crystalline melilite peak; measuring the X-ray diffraction peak intensity of the annealed sample for a standard peak; and determining the concentration of blast furnace slag in the sample by consideration of the weight loss resulting from annealing, the amount of the known quantity of the sample, the amount of the known quantity of the standard and the measured X-ray diffraction peak intensity of the melilite peak and the standard peak. Annealing a sample containing blast furnace slag at a temperature between about 800° C. and about 1000° C. results in the amorphous blast furnace slag converting to crystalline forms of melilite and anhydrite. A melilite X-ray diffraction peak is selected that has a minimal interference with other X-ray diffraction peaks of the remaining components of the sample and the standard. The standard is used to quantify the amount of melilite in the annealed sample. The standard is calibrated with annealed blast furnace slag to determine the relative peak intensities of the standard and the melilite. This calibration, along with the measured relative peak intensities, the weight loss from the sample and the amounts of standard and sample establish the amounts of blast furnace slag in the sample. Elemental silicon has been found to be a convenient standard because it rarely occurs naturally and it is not otherwise typically added to the slurries of the present invention.

The annealing temperature is lower than the melting point of the blast furnace slag, but sufficiently high to result in the crystallization of the blast furnace slag into melilite and anhydrite.

This method can be used to determine the amount of a pozzolan such as blast furnace slag in a slurry such as a drilling mud to an accuracy of within about 3% by weight of the sample.

DETAILED DESCRIPTION OF THE INVENTION

Figure 1:
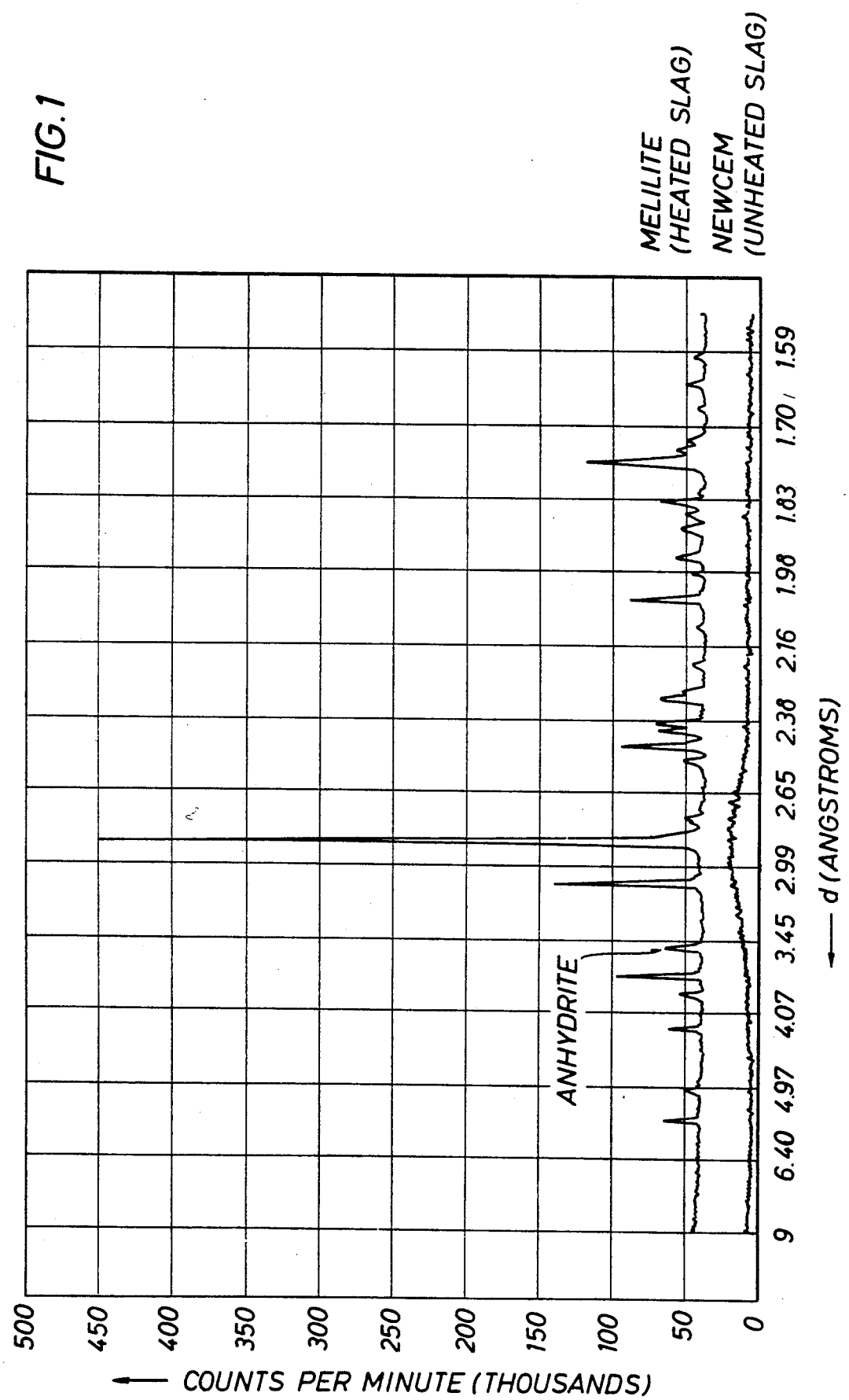
FIG. 1 is an X-ray diffraction pattern of amorphous blast furnace slag and of annealed slag.

X-ray diffraction analyses are typically performed by first grinding a sample into a fine powder (<44 μm). The fine powder is then spread evenly on a plate sample holder. X-rays are generated and directed at the sample powder over a varying range of incidence, usually by rotating the X-ray source in a semi-circle around the sample powder. X-rays diffracted at that varying angle of incidence are measured. X-rays will be diffracted to all angles from each atom in the sample crystal matrix, but random diffractions will destructively interfere with each other. Destructive interference will cause the diffracted X-rays to essentially cancel each other. At a particular diffraction angle, the angle being a function of distance between planes of atoms in the crystal matrix for any wavelength of X-rays, the diffracted X-rays will constructively interfere. The relationship between these variables is established by Bragg's Law as:

$$2d \sin \Theta = n\lambda \quad (1)$$

where
- d is the distance between planes of atoms,
- $\Theta$ is the angle of incidence of the X-rays measured from the plane of the sample,
- $\lambda$ is the wavelength of the X-rays, and
- n is a whole number.

A particular crystal matrix will provide constructive interference at a number of angles of incidence, each corresponding to a particular reoccurring distance between planes of atoms within the crystal. A crystal having a cubic symmetry would result in relatively few diffraction maxima. A crystal structure with lower symmetry would result in relatively more diffraction maxima. A mixture of different types of crystal symmetries would result in superimposed "fingerprints" of the individual crystal structures.

Diffracted X-rays are typically measured by detectors such as film, proportional, Geiger, scintillation, or semiconductor detectors. These are well-known in the art.

Relative intensities of peaks of an X-ray diffraction pattern may be used to determine relative amounts of materials in samples according to the following equation:

$$\frac{w_i}{w_j} = \frac{I_i}{I_j R_{ij}} \quad (2)$$

where:
- $I_i$ is the intensity of a particular diffraction peak for component i of the mixture,
- $I_j$ is the intensity of a particular diffraction peak for component j of the mixture,
- $w_i$ is the weight fraction of component i the mixture,
- $w_j$ is the weight fraction of component j the mixture, and
- $R_{ij}$ the reference intensity ratio for the diffraction peaks $I_i$ and $I_j$. This ratio can be determined experimentally by combining known amounts of components i and j and measuring the resultant intensities of the diffraction peaks.

$R_{ij}$ can be readily determined experimentally by mixing known quantities of the two components, measuring peak intensities for a particular peak from each component, and substituting into Equation 2.

The weight fraction of a crystalline component ($w_i$) in a sample can be determined using Equation 2 by determining $R_{ij}$ experimentally, mixing with the sample a known quantity of a standard ($w_j$), and measuring the ratio of the peak intensity of that standard to a peak from the crystalline components of interest. Elemental silicon is a preferred standard. Elemental silicon rarely occurs in nature and therefore could usually be used as a standard.

Peak intensities are defined as the integrated area under a peak in a plot of detected diffracted X-rays versus the angle of incidence. Digital recording of X-ray diffraction data and known methods to account for overlap of peaks are well-known in the art.

Amorphous materials in mixtures produce a broad curve of X-ray diffraction peaks because atoms lack long-range order as opposed to occupying well-defined atomic positions in a crystalline matrix. X-ray diffraction is therefore more ambiguous in analysis of amorphous materials.

Samples containing blast furnace slag are annealed to transform amorphous slag into crystalline materials. Blast furnace slag has been found to form, upon annealing, about two percent by weight anhydrite and about ninety-eight percent by weight melilite. Other types of slag or pozzolans may form other crystalline materials. The present process may be applied to these other pozzolans by determining the percentage of the slag of pozzolan which forms a particular identifiable crystalline material upon annealing. It is preferable that the slag or crystalline material be converted to essentially all crystalline material by the annealing process, but this is not essential. As long as a reproducible portion of the slag or pozzolan converts to crystalline material, a quantification of the slag or pozzolan in a slurry may be obtained.

The preferred pozzolan in the practice of this invention is a blast furnace slag, and the preferred blast furnace slag is NEWCEM, a material commercially available from Blue Circle Atlantic, Inc.

The annealing of the present process is necessary to convert the amorphous blast furnace slag to a structure that is quantifiable by X-ray diffraction. The annealing must be performed at a temperature below the glass transition temperature of the amorphous material. At temperatures near the glass transition temperature, glassy or liquid structures will tend to break apart at a rate as great as that at which they are formed. The annealing temperature, although below the material's glass transition temperature, must be elevated in order for crystallization to take place within a reasonable time. Typically, a temperature with the range of about 800° C. to about 1000° C. is acceptable.

The sample analyzed by the method of the present invention may be a slurry such as a drilling mud, completion fluid or workover fluid. The annealing is preferably performed by drying the sample first. Drying can be accomplished by holding sample at a temperature greater than about 100° C. to drive off liquid water. The liquid water would be quickly removed at higher temperature, but applying heat too quickly could result in splattering of the sample. In addition to driving off water, some carbonates will release carbon dioxide, and small amounts of hydrogen sulfides could be released from minerals, and hydrocarbons could degrade to methanes, ethanes, and oxidize to carbon monoxides and carbon dioxides. The sample must therefore be carefully weighed before and after annealing to determine the amount of sample lost during the drying and annealing.

After annealing, the sample will be ground to form a powder acceptable for analysis by X-ray diffraction. Annealed samples may be powdered using, for example, an agate mortar and pestle, or a Brinkmann impact grinder. A standard such as powdered elemental silicon is typically added to the powdered annealed sample. The weight ratio of standard to powdered sample is determined. The combined standard and annealed sample can then be homogenized by mixing with water in a vortex or Sonicator. The powder is then deposited on a porous disk by forcing the water through the disk by application of a positive pressure to the slurry above the disk. The disk is ready for X-ray diffraction analysis after the film of powdered sample and standard is dried. A Seifert-Scintag PADX powder X-ray diffractometer is an acceptable X-ray diffraction measurement apparatus. Peak intensities are measured, and weight fractions of a crystalline material formed from annealing the blast furnace slag is determined using Equation 2, above. The weight fraction of blast furnace slag in the sample, X, is then determined according to:

$$X = \frac{W_{MEL} + W_{ANH}}{W_{SX} + W_{LOSS}} \quad (3)$$

where $W_{MEL}$ and $W_{ANH}$ are the weights of the melilite and anhydrite ($W_i$ from equation 1) in the annealed sample as determined from Equation 2, $W_{SX}$ is the weight of the whole sample (the combined weight of the annealed sample and the standard)

$W_{loss}$ is the fractional weight loss of the sample resulting from the drying and annealing process.

EXAMPLE

FIG. 1 is an X-ray diffraction pattern collected on a Seifert-Scintag PADX powder X-ray diffractometer for a sample of annealed NEWCEM and NEWCEM that has not been annealed. The NEWCEM that has not been annealed displays an X-ray diffraction pattern typical of an amorphous material. It is a broad bell-shaped peak. The annealed NEWCEM displays an X-ray diffraction pattern of a mixture of about 2% by weight anhydrite and about 98% by weight melilite.

Figure 2:
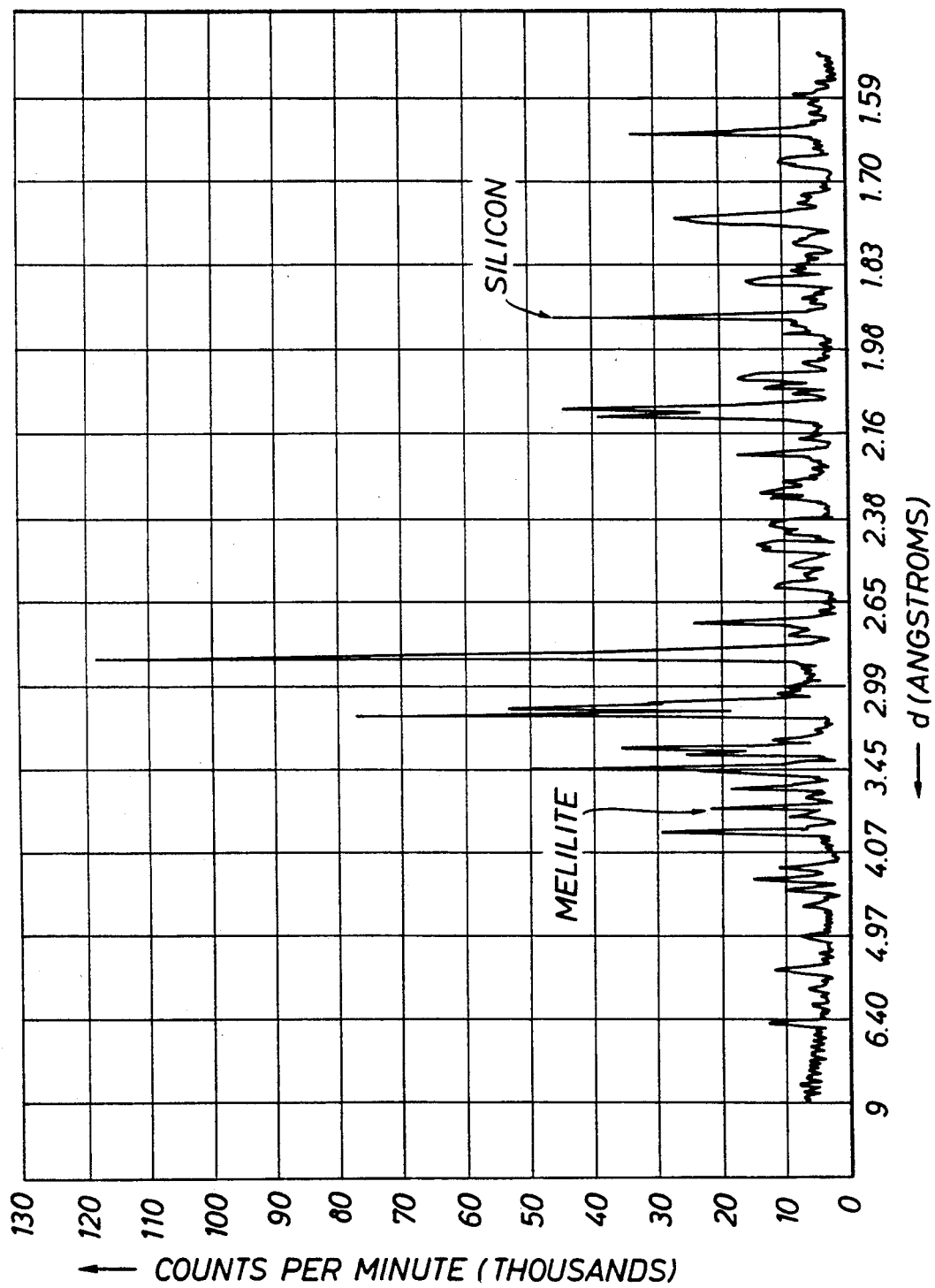
FIG. 2 is an X-ray diffraction pattern of an annealed sample of a drilling mud containing elemental silicon and blast furnace slag.

FIG. 2 is an X-ray diffraction pattern collected from an annealed sample of drilling mud containing 24 percent by weight NEWCEM. Elemental silicon was also added to the sample. About 3 mg of elemental silicon was added to about 40 mg of 44 mesh ground annealed sample. The presence of elemental silicon is evidenced by a peak at 1.92Å. A melilite peak at 3.71Å is useful to quantitatively determine the amount of NEWCEM in the sample. Weight loss upon drying and annealing the slurry sample was 11% by weight. The percent NEWCEM determined to be in the slurry sample by the method of the present invention was determined to be 24% by weight, the same as the percent NEWCEM added to the sample. In two other experiments, slurries containing 23 and 29 percent by weight of NEWCEM were prepared. The percent NEWCEM determined by the method of the present invention were 25 and 32 percent by weight, respectively.

This experiment demonstrated the viability of determining the amount of an amorphous material such as NEWCEM in the slurries such as drilling muds by the method of the present invention.

The foregoing description of the invention is explanatory of the invention, and various changes in details of the described invention may be made within the scope of the following claims.

We claim:

1. A process to determine the weight fraction of amorphous blast furnace slag in a sample comprising the steps of:
   providing a quantity of a sample of known weight containing amorphous blast furnace slag;
   annealing the known quantity of the sample at a temperature of between about 800° C. and about 1000° C. for a time period of about two hours or greater thereby converting the amorphous blast furnace slag to a crystalline composition comprising melilite;
   weighing the annealed sample and determining the amount of weight loss ($W_{Loss}$) of the sample resulting from the annealing of the sample;
   adding a quantity of a standard of known weight ($w_j$) to the annealed sample;
   measuring the X-ray diffraction peak intensity of the combined annealed sample and standard for a crystalline melilite peak ($I_i$);
   measuring the X-ray diffraction peak intensity of the combined annealed sample and standard for a standard peak ($I_j$); and
   determining the weight fraction of blast furnace slag (X) in the sample by using the equation $$\frac{w_i}{w_j} = \frac{I_i}{I_j R_{ij}}$$

to corrolate relative intensities of x-ray diffraction peaks with relative amounts of material in the sample, and by using the equation $$X = \frac{W_{mel} + W_{Anh}}{W_{Sx} + W_{Loss}}$$

for relating relative amounts of the materials to the weight fraction of the blast furnace slag.

2. The process of claim 1 wherein, prior to annealing, the known quantity of the sample is dried by heating the sample to a temperature greater than about 100° C. until water does not evolve from the sample.

3. The process of claim 1 wherein the sample is a blast furnace slag containing slurry selected from the group consisting essentially of drilling fluid, workover fluid and completion fluid.

4. The process of claim 1 wherein the standard is silicon.

5. The process of claim 3 wherein the standard is silicon.

6. The process of claim 5 wherein the sample is drilling fluid.

* * * * *